United States Patent [19]
Baumgarten

[11] 3,980,198
[45] Sept. 14, 1976

[54] EXPANDABLE CONTAINER

[75] Inventor: Carl B. Baumgarten, Houston, Tex.

[73] Assignee: Gomco Surgical Manufacturing Corporation, Buffalo, N.Y.

[22] Filed: July 7, 1975

[21] Appl. No.: 593,372

Related U.S. Application Data

[63] Continuation of Ser. No. 420,890, Dec. 3, 1973, abandoned.

[52] U.S. Cl. .............................. 220/8; 128/214 R; 128/214 B
[51] Int. Cl.² ..................... A61M 1/00; B65D 11/18
[58] Field of Search .......... 220/8; 128/214 R, 214 B

[56] References Cited
UNITED STATES PATENTS

| | | | |
|---|---|---|---|
| 2,887,243 | 5/1959 | Murdock | 220/8 |
| 3,111,153 | 11/1963 | Sonka | 150/48 |
| 3,114,468 | 12/1963 | Quase | 220/8 |
| 3,207,298 | 9/1965 | Wilson | 150/48 |
| 3,211,368 | 10/1965 | Shanley | 128/214 R |
| 3,329,298 | 7/1967 | Demas | 220/8 |
| 3,391,818 | 7/1968 | Hariston | 220/44 B |
| 3,578,415 | 5/1971 | Hiltz | 220/8 |

Primary Examiner—George E. Lowrance
Attorney, Agent, or Firm—Kenneth H. Johnson

[57] ABSTRACT

An expandable container comprising two or more slidably engaged sections which are adapted to telescope into a compact unit for storage, but for use the sections are extended to provide two to four times the volume capacity of the closed or unextended container. The fluid and vacuum integrity of the system is obtained by a closure means at each juncture of telescoping sections such as flexible film which is sealed over junctures of the sections, thus leaving the sections free to slide in and out. The expandable container has found particular utility in vacuum liquid collection systems employed by hospitals.

7 Claims, 8 Drawing Figures

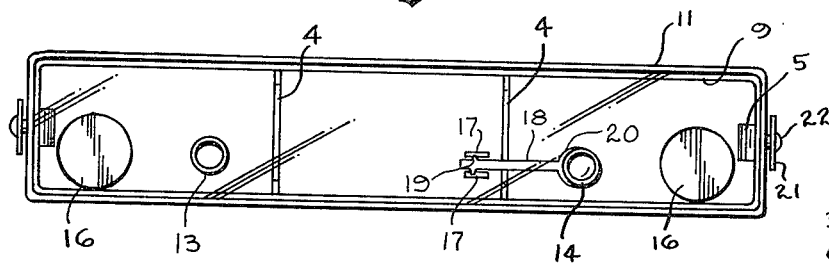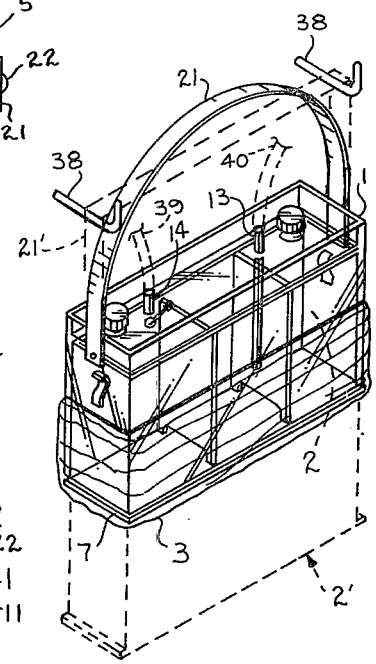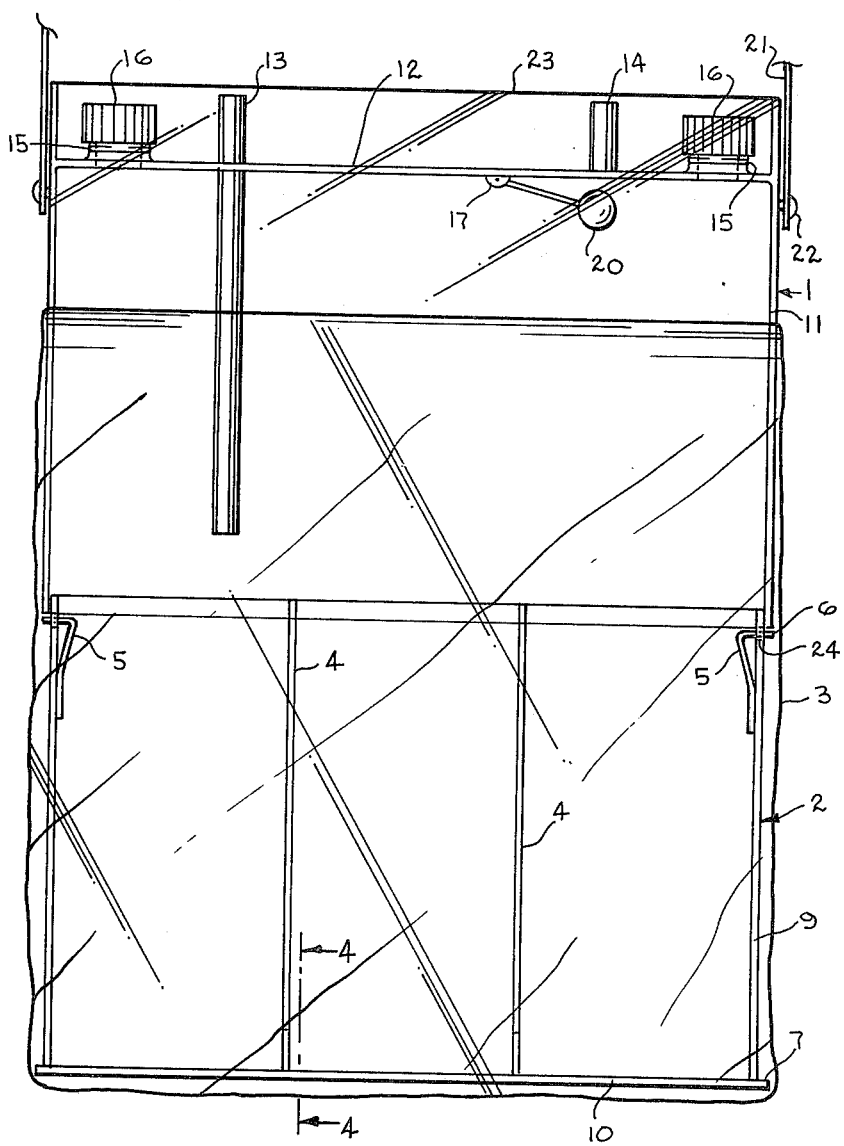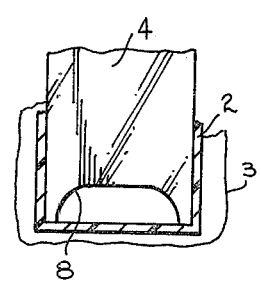

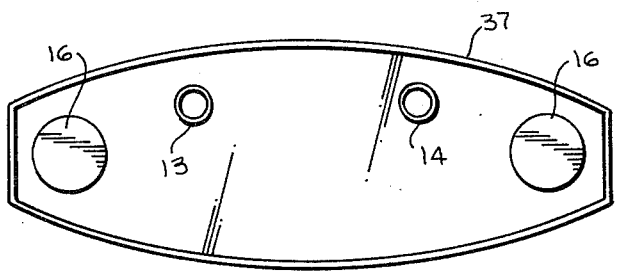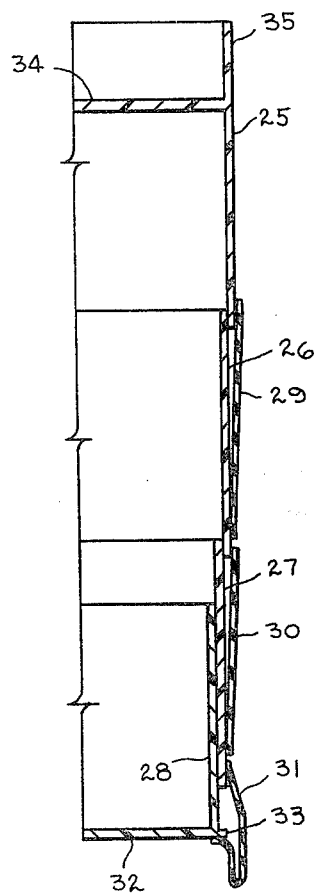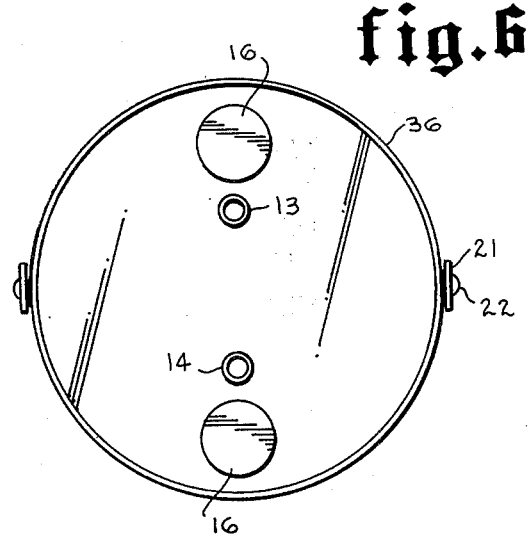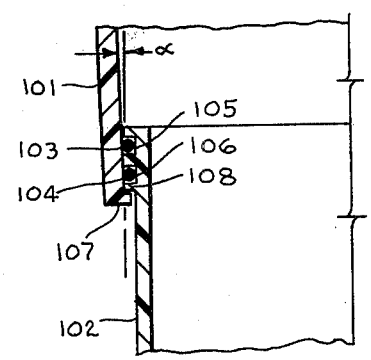

EXPANDABLE CONTAINER

This application is continuation of Ser. No. 420,890, filed Dec. 3, 1973, now abandoned.

BACKGROUND OF THE INVENTION

The present invention relates to a fluid collection system, and in particular to a vacuum collection system.

Recently the cost of hospital services has sustained substantial inflationary increases. The rise in hospital costs can be attributed to increase in the cost per square foot of hospital space and rising labor costs.

It is very common in the care of hospital patients that some manner or type of fluid drain or collection system will be employed. Generally such collection systems are used to collect body fluids which would be detrimental to the patient if not removed. To insure such collection the collection is made by the use of a vacuum system. The fluids being withdrawn are desirably collected for examination, analysis or for volumetric measurement which can be used as determinates of the condition of the patient.

Presently vacuum collection is generally carried out in glass containers which are stored and reused. This presents several potential problems, principal among which are breakage and high cost. Since these collection containers are employed in a vacuum system, they must have sufficient rigidity to avoid collapsing the container and more importantly to provide the absolute integrity needed for the system. To achieve the requisite degree of rigid strength and observability, it is the general practice to employ glass containers, e.g., Pyrex or other high temperature glass. Pyrex containers provide the vacuum integrity and dependability required and also the clear or translucent container for visual observation of the specimen being collected.

Since the fluid collection system must usually operate for substantial periods with only periodic examination, the container must be of a sufficiently large volume to assure that there will be an adequate collection space for the specimen. Generally gallon containers are employed, regardless of the expected size of the specimen. Very frequently gallon containers are employed in series if larger volumes are anticipated or as a safety measure. The problem presented is one of storage space. Gallon containers, e.g., usually round bottles or jugs, can occupy a substantial amount of the area allotted for storage within a hospital or clinic.

A second disadvantage of the usual type of container employed is the trouble and expense of clean-up and sterilization. Because of the requisite strength of the containers, their manner of construction or manufacture is substantial and hence expensive. Thus it is necessary to reuse the containers in order to obtain an adequate utilization as based on the cost. Furthermore, disposal of the present containers, because of their size and nature, could present problems. Generally recycle or reuse is a very admirable characteristic of an article, however, in the hospital environment, the amount of labor necessary to recycle the containers far offsets in money and rising hospital costs the recycle value. The fragile nature of glass is also a problem in shipment, handling and use.

It is an object of this invention to provide a collection system which will require less storage space, yet provide the same collection capacity as prior systems. It is a further object of this invention to provide a collection system which inherently will be less costly to manufacture and will afford the option of disposable use.

It is another object of this invention to provide a collection system with an expandable capacity. It is another object of the present invention to provide a means to locate the collection system at a convenient level for visual examination of the contents thereof.

These and other objects will be eminently clear from the following discussion of the invention and descriptions of the drawings and embodiments thereof.

SUMMARY OF THE INVENTION

Briefly stated the present invention is in a fluid collection system comprising an upper section forming an enclosed upper compartment having ingress and egress means thereto, a lower section forming a lower compartment communicating with said upper section and slidably engaged therewith, means to maintain said sections in an extended condition while slidably engaged, and means for hermetically sealing said sections together for maintaining a vacuum in the space enclosed by said sections.

Generally the present invention will consist of two or more sections which are slidably engaged whereby the sections will telescope so that the capacity of the container formed can be increased for use, but which will collapse one inside the other for storage and shipment, thus reducing the space required when not in use but providing at least as much volume as the containers presently in use.

The container can be made of a variety of materials, including the rigid or semi-rigid polymers or the like and can be manufactured in a variety of shapes and sizes. Preferably rigid polymeric material such as polyvinyl chloride or methylmethacrylate with a thickness of about 1/32 to 1/16 of an inch would be used. The material may be at least translucent and a substantially clear, uncolored material is most preferred so that the specimen can be readily observed for diagnostic signs.

In order to employ a telescoping arrangement as described in a vacuum system, a means must be provided to seal the various sections together. In one embodiment of the present invention this has been very simply achieved by sealing a continuous air-impervious flexible film over the juncture of the slidably engaged sections. There are several means of achieving this, including employing the continuous flexible film as an enclosed bag which is sealed onto the upper section. The bag itself has no structural strength relative to the vacuum, and the structural rigidity is provided by the lower sections of the collection system. Another method is to hermetically seal the flexible film in the form of a sleeve onto each section.

The continuous, air-impervious flexible film can be any material which meets these functional requirements and which can be hermetically sealed. Generally it is contemplated various polymeric clear or translucent films of 1–6 mil thickness such as polyethylene, polypropylene, polybutene, polyesters or the like may be employed. The film can be sealed by any of the methods known in the prior art, for example, solvent cements, heat sealing, adhesives, sonic fusion and the like. In addition the film may be reinforced for example with nylon or polyester fibers.

Another particular feature of the invention is the provision of a means to retain the sections in the extended position when in use. This element was found necessary since without it the vacuum within the container created from the sections will tend to collapse the sections into the closed or nested position.

When in use the vacuum or suction is maintained within the enclosed areas of the section because of the sealing effect of the flexible film which covers the joint of each section with its adjacent section and hermetically seals each joint. Thus the same vacuum integrity is obtained with the inexpensive, rugged, compact collection system of the present invention as with the prior Pyrex bottles for example.

It can be readily appreciated that there can be more than an upper and lower section. The intermediate sections will be open for communication with the sections adjacent thereto. Normally this means the intermediate sections will have neither a top nor bottom, but will consist of a peripheral wall.

Very conveniently each section below the upper section seats inside of the immediately preceding section. The seating is obtained by sliding the section into the section above it. The flexible film does not restrict the sliding location and relocation of the sections from open to closed or vice versa. The sections are close-fitting, which is an aid in that flexible film is, thus, not subjected to the suction stress over an opening or other space which might create a site of structural weakness in the system. When a single continuous flexible film in the form of a bag is used as the means of hermetically sealing the joints, the bag is attached to the upper section and is outside of all of the sections below the upper section. In the closed or nested position the bag, if used, may be folded and secured to the nested sections for storage.

The total capacity of fully extended sections can vary but will usually be for about one gallon or from about one-half to two gallons. The collection system can be employed in the closed or partially extended configuration so that all of the benefits are achieved. It is contemplated that each section of the system may have a specific volume, for example, in a two section system each section may have a capacity of approximately one-half gallon, so that the fully extended system will have a capacity of about one gallon in use but only one-half gallon in storage.

Another embodiment contemplates a series of four sections, each having the capacity of about one quart, which may be used as indicated in the fully or partially extended configuration for collection of from one quart up to a gallon.

In order to facilitate diagnostic observation there can be volume indica on the sections or the flexible film.

In order to employ the present collection system, it is provided with at least two openings in the upper section. One of the openings connects with a suction system, such as a hospital suction pump or a community vacuum system. The other opening is connected to the patient for drainage. In addition to these openings there may be additional openings, with closures thereon, for removing collected fluids without disconnecting the collection system from the patient or the vacuum source.

The collection system of the present invention will usually be used with rather moderate vacuums because of the nature of the use. Suitable low negative pressures would be from around 10 to 60 inches of mercury and will generally be around 30 inches of mercury. Needless to say the pressure is very accurately controlled and must be maintained by the components of the system.

Another feature of the present invention is a means for attaching the collection system at a level above the floor where it can be more conveniently observed. It is possible with some hospital vacuum pumps, such as the Gomco Thermotic 765 A or Surgical Section Unit 929 to hang the collection system on the pump apparatus with a handle attached to the collection system.

It is an advantage of the present collection system that it is compact for storage but expandable to a larger capacity or capacities. Another advantage of the present invention is that it may be fabricated by a number of methods from inexpensive, damage-resistant materials. Another advantage of the invention is that it can be fabricated in a variety of shapes and combinations of section sizes.

It is a feature of the collection system that it has means for hermetically sealing the various sections at all times. Thus it is a further feature and advantage of the present collection system that it may be employed in a fully extended form or in a closed or partially extended form. It is a further feature of the present system that it is suitable for use in a vacuum system. It is another feature that the system may have a means for positioning the container at a level above the floor for better visual observation of the fluids collected.

In another aspect, the present invention relates to a container comprising an upper section forming an enclosed upper compartment having an opening therein, a lower section forming a lower compartment communicating with said upper section and slidably engaged therewith, means for maintaining said sections in an extended condition while slidably engaged, and means for forming a fluid-tight seal between said sections.

In addition to use in hospital suction systems, the present container can be employed as any other container and is particularly useful where the container is stored for emergency use or for campers or the like. In such a use only one opening may be required at the top.

These advantages and features of the present invention, as well as others, will become apparent from the following detailed description of the invention, the drawings and the invention in relation to the drawings.

Like characters of reference indicate corresponding parts in the figures of the drawings. The present invention will be better understood by reference to the drawings and the detailed description thereof.

DRAWINGS

FIG. 1 is an isometric view of an embodiment of the present collection system in a closed configuration.

FIG. 2 is a cross sectional elevation of the embodiment shown in FIG. 1 in an extended configuration.

FIG. 3 is a top view of the embodiment shown in FIG. 1.

FIG. 4 is a cross sectional view taken along 4—4 of FIG. 2.

FIG. 5 is a cross sectional view of an alternate configuration showing four sections.

FIG. 6 is a top view of an alternate embodiment having a circular cross section.

FIG. 7 is a top view of an alternate embodiment having a modified elliptical cross section.

FIG. 8 is a cross sectional view of an alternative embodiment having a circumferential gasket.

DETAILED DESCRIPTION OF PREFERRED EMBODIMENTS

Referring to FIG. 2 the collection system or container of the present invention can be seen in the "open" or extended configuration. In this embodiment the collection system is comprised of two sections, upper section 1 and lower section 2, slidably engaged. The lower section 2 is adapted to slide inside of section 1. The upper section 1 consists of a vertical wall 11 having a particular cross section or shape which, as shown by reference to FIG. 3, is rectangular. The wall 11 is hermetically attached to top member 12 and is open at the lower end. Seated inside of the lower end of wall 11 is the vertical wall 9 of lower section 2 which has the same cross section as upper wall 11, but with outside dimensions approximately the same as the inside dimension of wall 11 of upper section 1. Reference to FIG. 1 will show the collection system of FIG. 2 in the closed or collapsed configuration.

Referring again to FIG. 2 wall 9 is hermetically sealed to bottom member 10 which has a peripheral shoulder 7 which seats against the lower edge of wall 11 when the lower section 2 is fully seated in upper section 1 in the closed position.

The shoulder 7 serves to prevent lower section 2 from going too far into the upper section 1, making it difficult to grasp and pull out for use in the extended configuration as shown in FIG. 2. The shoulder 7 also provides a convenient point to grasp when the lower section 2 is slid out to the extended position.

Attached inside of the lower section 2 on wall 9 and near the upper edge thereof are the latches 5. The upper ends 6 of the latches 5 are aligned with slots 24 in wall 9. Each latch 5 is a resilient material biased so as to force the end 6 through slot 24 when there is no force holding it back. Thus when the lower section 2 is seated inside the upper section 1 in a closed configuration the wall 11 holds end 6 back; however when the lower section 2 is slid down to the extended position with the slot 24 below wall 11, the end 6 is biased out. When the latch 5 is in this position the end 6 is seated against the lower edge of wall 11, and lower section 2 can not be inadvertently pushed or drawn back into the closed position shown in FIG. 1. This is a particularly important feature when the collection system is employed with a vacuum, for the lower section 2 will tend to be pushed back into the upper section 1 by the vacuum in the container space formed by the two sections.

Hermetically attached to upper section 1, about wall 11 in an air and liquid impervious flexible film 3, which in this embodiment is an air tight plastic bag. The bag 3 provides in this embodiment not only the air tight seal for the juncture of the two sections but also serves to hold the lower section 2 in the engaged position shown. In an alternate embodiment (not shown) the two sections are held in the extended position by means of a slot in wall 11, which slot will align with the slot 24 in wall 9 thus allowing the end 6 of latch 5 to engage the wall 11, thereby locking the two sections in place.

In order to return the lower section 2 to the closed position in either embodiment described above, the latch 5 is depressed until end 6 is within the slot 24 while a slight upward pressure is applied to the lower section 2 while the upper section 1 is maintained in a fixed position.

In addition to the latch 5, there may be positioned in the lower section 2, support members or walls 4 which also provide some support to the upper section 1 because of the engagement of the two sections. In order to provide communication throughout the entire lower section 2, the support members 4 have opening 8 as can be seen by reference to FIG. 4. The support members 4 are not essential but do provide an additional degree of reliability of the collection system with vacuums and structurally, they allow lighter walls 9 and 11. Other known techniques can be used such as ribs or vanes in the walls 9 and 11 to reduce wall thickness and weight.

Again in FIG. 2 the upper section 1 has located on the top member 12 an inlet 13 and an outlet 14, both adapted to have tubes attached thereto. The inlet 13 comprises an elongated tubular member which extends almost to the lower edge of the wall 11. The elongated tube 13 is a preferred refinement and insures that fluids flowing in through inlet 13 are not drawn inadvertently into the outlet 14 by the force of the suction. The inlet 13, however, need only provide an ingress into the container. In the embodiment shown in FIG. 2 a further improvement is the safety valve juxtaposed below the outlet 14. The safety valve is comprised of arm 18 pivotally mounted by means of nibs 19 in corresponding indentions in projections 17 attached to top member 12. Located at the opposite end of the arm 18 from the pivot is a flotation ball 20, which is operably aligned to seat into outlet 14 when the fluid rises toward the top member 12 and block the outlet so that the fluid will not pass into the vacuum source. In some applications, however, as when the collection system is one of several units in series the safety valve is not desirable and would be omitted in all but the last collection system in the series.

A further feature which increases the versatility of the present collection system is the provision of one or more auxiliary openings in the top member 12. In the embodiment of FIG. 2 there are provided two threaded necks 15 with screw cap closures 16, which provide an air tight seal. These removable closures 16 allow removal of the collected specimen without disruption of the system, by pouring the speciment out through the opened neck 15.

A strap 21 is attached to the upper section 1 by rivets 22. The strap 21 provides a convenient means to carry one or more of the collection systems by hand. A particular utility for the strap 21 is seen by reference to FIG. 1 wherein the strap as mounted on prongs 38 is depicted by phantom strap 21'. Prongs similar to those illustrated are found on some hospital pumps such as those previously mentioned. The strap 21 may be hung on any convenient prong, handle or the like. The purpose being to remove the collection system from the floor and to put it out of the way. This procedure can also put the collection system into a better position for observation of the fluids collected. The strap can be made of flexible or semi-flexible material such as cloth, leather or nylon, polypropylene or the like.

Adjacent to the top member 12 is an extension of wall 11 which forms a protective enclosing wall 23 around the top member 12. The purpose of this protective wall 23 is to provide a degree of protection to the elements projecting from the top member 12, particularly during shipment and storage.

Referring now to FIG. 5 there is shown an embodiment wherein in addition to upper section 25 and lower section 28 there are two intermediate sections 26 and 27. Each of the lower sections is slidably engaged in the preceding section. The upper section 25 has a top member 34 and a protective wall 33 is provided. The lower section 28 is enclosed with a bottom member 32 which has a shoulder 33 serving the same purposes as shoulder 7, previously described in FIG. 2.

Each adjacent section in FIG. 5 is hermetically sealed to the next section by means of a continuous flexible film, 29, 30 and 31 circumventing the collection system. In FIG. 5 the four section collection system is only partially extended. The remainder of system may be substantially the same as previously described.

FIG. 6 shows the same collection system as depicted in FIGS. 1–5, but in a cylindrical configuration as indicated by the circular cross section of wall 36. Referring to FIG. 7 another configuration is depicted having a configuration similar to that of FIG. 1 with bowed out sides 37. The cross section of the top view can be characterized as elliptoid, i.e., being an ellipse with the ends cut off. These or practically any other shape can be used, limited only by fabrication cost and reason. Each of the sections will have cooperating configuration with the other sections of the collection system. Similarly each of the collection systems may have the various modifications described above.

In order to provide a clearer understanding of the invention as used in a collection system, a brief description of the setup of the device of FIG. 1 will be given. In FIG. 1 a preferred embodiment in use is depicted. For example if the present container is to be used with a portable vacuum pump, such as the Gomco Thermotic 765 A*, there are projections, such as prongs 38, located thereon. The strap 21 is stretched over the projections (prongs) 38, as shown by phantom strap 21'.

*Gomco Manufacturing Company, Buffalo, New York

Thus positioned it is a simple matter to extend the container to its full capacity by grasping shoulder 7 and pulling it downward to the position indicated by phantom section 2'. The container will now preferably be in the configuration shown in FIG. 2.

Referring again to FIG. 1, the inlet 13 is connected by means of tube 39 to the patient and the outlet 14 is connected by means of tube 40 to the suction of the pump. The system is now ready for operation.

As noted above in use as a collection system, the present container must have transparency or at least translucency; however, when used in other applications, translucency may be unimportant and opaque materials may be used in the construction thereof.

FIG. 8 shows an embodiment wherein the sealing of the sections in extended position is achieved by a circumferential gasket. In the figure, upper section 101 and lower section 102 are shown in the fully extended position. The inwardly projecting flange 107 seats against the outwardly projecting shoulder 108. The circumference of the upper section 101 is smaller at the end of the section which is adjacent the gaskets 103 and 104 in the extended position shown. The gaskets 103 and 104 are a resilient material such as closed cell neoprene now available on the market. The small diameter can be seen by reference to line $\alpha$, which is the projection of the shoulder 108 of the lower section. It can be seen that the portion of upper section 101 above that in contact in the extended position has a circumference greater than shoulder 108, thus allowing the sections to move easily into the extended configuration. However as the end portion of upper section 101 comes into juxtaposition to shoulder 108 its smaller circumference, which is substantially the same as line $\alpha$, compresses the resilient gaskets and forms an air tight seal.

One gasket would operate, and two are merely a safeguard. The gasket 103 and 104 are set in annular grooves 105 and 106 respectively in shoulder 108 and are annular about the circumference of lower section 102, however they project outward when the larger portion of upper section 101 is juxtaposed thereto. They are shown in their compressed state in FIG. 8. This mode of sealing the sections together will operate best when there are no sharp angles to be sealed. For example, the circular configuration shown in FIG. 6 would be well adapted to this sealing mode or the configuration of FIG. 7 with the corners rounded off. The other features previously described are also adapted to this sealing embodiment.

The invention claimed is:

1. A container for collecting liquids under vacuum comprising an upper section forming an upper compartment having an opening therein and a tube extending from said opening into said upper section for liquid ingress, an opening in said upper compartment for connection to a vacuum source, a lower section forming a lower enclosed compartment communicating with said upper section and slidably associated with said upper section, a latch attached to one of said sections and adapted to engage a portion of another section to lock said sections in an extended position relative to each other while slidably associated, said sections having structural rigidity, a fluid tight seal formed by a continuous flexible film sleeve position externally about said container over the juncture of said sections, said sleeve being hemetically sealed to each section.

2. The container according to claim 1 comprising at least one section positioned between said upper and lower sections, slidably associated with said upper and lower sections and communicating therewith.

3. The container according to claim 2 wherein said film is a polymeric material having a thickness of from about 1 to 6 mils.

4. A container for collecting liquids under vacuum comprising an upper section forming an upper compartment having an opening therein and a tube extending from said opening into said upper section for liquid ingress, an opening in said upper compartment for connection to a vacuum source, a lower section forming a lower enclosed compartment communicating with said upper section and slidably associated with said upper section, a latch attached to one of said sections and adapted to engage a portion of another section to lock said sections in an extended position relative to each other while slidably associated, said sections having structural rigidity, a fluid tight seal formed by a continuous flexible film bag positioned externally about said container over the sections of said container and hemetrically sealed to said upper section.

5. The container according to claim 4 having at least one section intermediate between the upper and lower sections and slidably associated therewith, said upper and lower sections communicating through said intermediate section.

6. The container according to claim 4 wherein said film has a thickness of from about 1 to 6 mils.

7. The container according to claim 4 wherein a safety flotation valve is juxtaposed below said opening for connection to a vacuum source.

* * * * *